United States Patent [19]

Armistead

[11] Patent Number: 4,852,131
[45] Date of Patent: Jul. 25, 1989

[54] COMPUTED TOMOGRAPHY INSPECTION OF ELECTRONIC DEVICES

[75] Inventor: Robert A. Armistead, Los Altos Hills, Calif.

[73] Assignee: Advanced Research & Applications Corporation, Sunnyvale, Calif.

[21] Appl. No.: 193,439

[22] Filed: May 13, 1988

[51] Int. Cl.⁴ .............................................. H05G 1/60
[52] U.S. Cl. .......................................... 378/4; 378/17; 378/58
[58] Field of Search ....................... 378/4, 58, 901, 17; 364/414

[56] References Cited

U.S. PATENT DOCUMENTS

| | | | |
|---|---|---|---|
| 3,454,762 | 7/1969 | Vollmer | 378/58 |
| 3,573,455 | 4/1971 | Suierveld | 378/58 |
| 3,889,122 | 6/1975 | Fletcher | 378/58 |
| 3,995,162 | 11/1976 | Peterson | 378/58 |

*Primary Examiner*—Craig E. Church
*Attorney, Agent, or Firm*—Rosenblum, Parish & Bacigalupi

[57] ABSTRACT

Computed tomography inspection apparatus and method of inspecting electronic devices and features of PCBs/PWBs, such as solder bonds, tracings and vias. The system scans radiation passed through the devices in thin slices and detects attenuated radiation from which it generates data representing slice images with high resolution. The detected image data are analyzed automatically by an image data analyzer which receives model data against which it compares and evaluates the detected image data.

9 Claims, 8 Drawing Sheets

FIG_ 1

FIG_ 2

FIG_ 3

SOLDER BOND
INSPECTION

FIG. 11

EVALUATING & REPORTING

FIG. 12

COMPUTED TOMOGRAPHY INSPECTION OF ELECTRONIC DEVICES

BACKGROUND OF THE INVENTION

1. Field of the Invention

The present invention relates generally to printed circuit or wiring board inspection techniques, and more particularly to a technique using X-rays for inspecting solder bonds and traces on such boards.

2. Discussion of the Prior Art

Integrated circuit (IC) devices formed in semiconductor chips are normally encapsulated in ceramic or plastic packages which provide input/output (I/O) pins for connecting the IC terminals to conductive traces to circuits outside of the packages. Conventional IC package pins project from the sides of the package for insertion into holes in a printed circuit board (PCB) or printed wiring board (PWB), where the pins are eventually soldered to conductive traces printed on the board surface around the holes. Recently, however, there has been a trend towards using surface mounted device (SMD) packages having flush I/O leads for being soldered directly onto flat contact pads on the surface of a PCB, rather than having conventional projecting I/O pin leads. SMD packages are smaller and can be mounted on both the top and bottom sides of PCBs, but disadvantageously depend upon their solder bonds ("joints") to mechanically retain the SMD on, as well as electrically connecting it to, the PCB. Packaged I.C. devices assembled on PCBs must withstand and function under various thermal and mechanical stresses. Electrically satisfactory solder bonds may nonetheless be mechanically unsatisfactory, and therefore need to be inspected for such characteristics as quantity, shape and density of solder. In the procedures of positioning SMD packages on boards and of soldering I/O leads to trace contact pads, packages can be placed or shifted out of their proper positions, causing the I/O leads to miss their trace contact pads, or to touch or form bridges to other contact pads. The solder-applying ("screening") mechanism can apply too much or too little solder, or can be misregistered with the board and apply solder off of contact pads. Bad solder paste, inactive flux, or dirty board surfaces can prevent solder from adhering to the leads and/or to the contact pads, and instead form stray solder bridges, wicks, balls, thickenings, delaminations, voids, cracks, inclusions of foreign material, etc. Following the solder screening process, incompletely removed flux can gradually corrode and cause failure of bonds or adjoining components.

Conventional IC packages with projecting I/O pins soldered into holes in circuit boards have been visually inspected for mechanical flaws under optical microscopes. However, increasingly complex and miniaturized very-large-scale integrated (VLSI) and very-high-speed integrated (VHSI) circuits require more (in the range of 84 to 240) I/O leads, which must be spaced relatively closely along the periphery of the packages. In addition, many SMD packages have large numbers of I/O leads requiring solder bonds arrayed beneath the package where they are inaccessable to conventional visual or infared inspection techniques, making the bonds difficult to examine.

Figure 1:
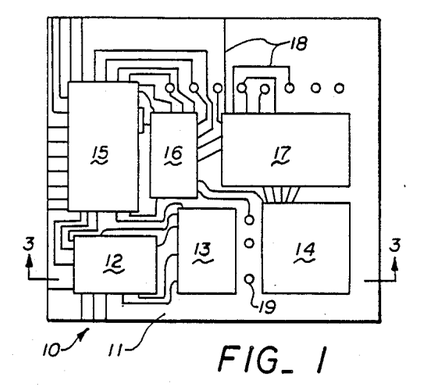
FIG. 1 is a top view of a printed circuit board populated with surface mounted devices.

FIG. 1 shows a top view of a printed circuit (or printed wiring) board 10 with an upper surface 11 on which SMDs 12 through 17 have been mounted. SMD packages 12 through 17 conceal their underside I/O leads. FIG. 1 also shows the top of a via hole 19 passing vertically through board 10.

Figure 2:
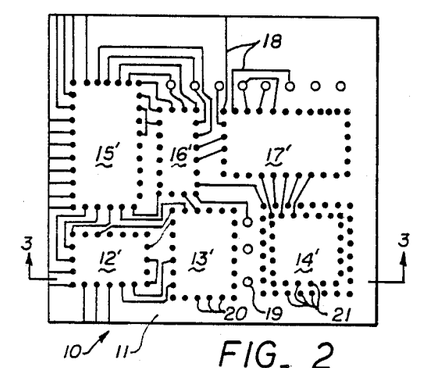
FIG. 2 is a top view of a circuit board as in FIG. 1 but without SMDs mounted on the surface and showing lead pads on the board to be connected by solder bonds to I/O leads of SMDs, and showing tops of via openings which pass vertically through the circuit board.

FIG. 2 shows a top view of the FIG. 1 board 10 with SMDs 12 through 17 removed from areas 12' through 17' to show the I/O lead contact pads 20 which would be visually inaccessible in actual SMD populated boards. A so-called "area array" package 14 has on its underside a large number of I/O leads (not visible) arranged in concentric ranks with outer ranks overlapping and concealing inner ranks.

Figure 3:
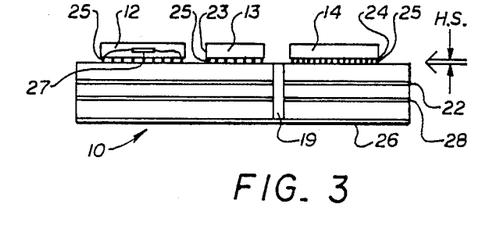
FIG. 3 is a cross-section taken along line 3—3 through the circuit board of FIGS. 1 and 2, showing multiple layers of the board, a vertical via through the board, an IC die attachment bond inside of a SMD package, and some of the solder bonds between SMD leads and conductive trace pads on the top surface of the circuit board.

FIG. 3 is a vertical cross section taken along FIG. 1 and FIG. 2 lines 3—3 through multiple-layer board 10, through vertical via 19, through conductive traces 22 and ground plane 28 sandwiched between layers, and through SMDs 12-14 mounted on the board surface 11. Solder bonds 25 may be formed (not shown) on the underside 26 of PCB 10. FIG. 3 also shows a die attach bond 27 holding the underside of an IC chip or "die" to the inside floor of SMD package 12. Improper formation or differential expansion of the die, attaching epoxy and/or lead frame can cause delamination of die attach bond 27, comprising the heat-sink function of board 10.

Solder bond interiors have been radiographed ("x-rayed") as disclosed in U.S. Pat. Nos. 3,454,762, 3,889,122, and 3,995,162. These prior art techniques pass X rays perpendicularly through the plane of solder bonds or other features of electronic devices to be examined. However, images of features happening to be in-line with other features in the path of the X-rays are superimposed and indistinguishable in the X-ray projection radiograph. Device feature inspections by infrared and ultrasonic techniques have been tried, but are not well suited for inspecting hidden solder connections 25. Infrared techniques cannot inspect a bond that cannot be seen, and ultrasound techniques only provide two-dimensional images of three-dimensional objects and therefore experience superposed images, do not have sufficient contrast resolution to precisely measure dimensions or density, and do not provide quantitative information.

A lack of adequate non-destructive examination (NDE) procedures has precluded inspecting and using some advanced IC packages with capacities to support higher I/O lead requirements. There remains, therefore, a need for a technique of non-destructive examination of visually inaccessible solder bonds or features of electronic devices to provide quantitative, high-resolution representations of defect conditions.

SUMMARY OF THE PRESENT INVENTION

It is therefore a primary objective of the present invention to provide means and a process of non-destructively inspecting and generating feature image data of mechanical/electrical interconnections of electronic devices to printed circuit or wiring boards.

Another objective is to provide means and a process for automatically analyzing generated image data to identify possible defect conditions in device interconnections.

Briefly, a preferred embodiment of the present invention provides a computed tomography (CT) system with improved means capable of scanning radiation in thinner slices through device interconnections and capable of detecting attenuated radiation from which to generate data representing slice images with a higher resolution. The CT system image data are analyzed automatically according to the invention by providing image data analyzing means which receives model data against which to compare and evaluate inspection image data.

DETAILED DESCRIPTION OF THE PREFERRED EMBODIMENTS

Figure 4:
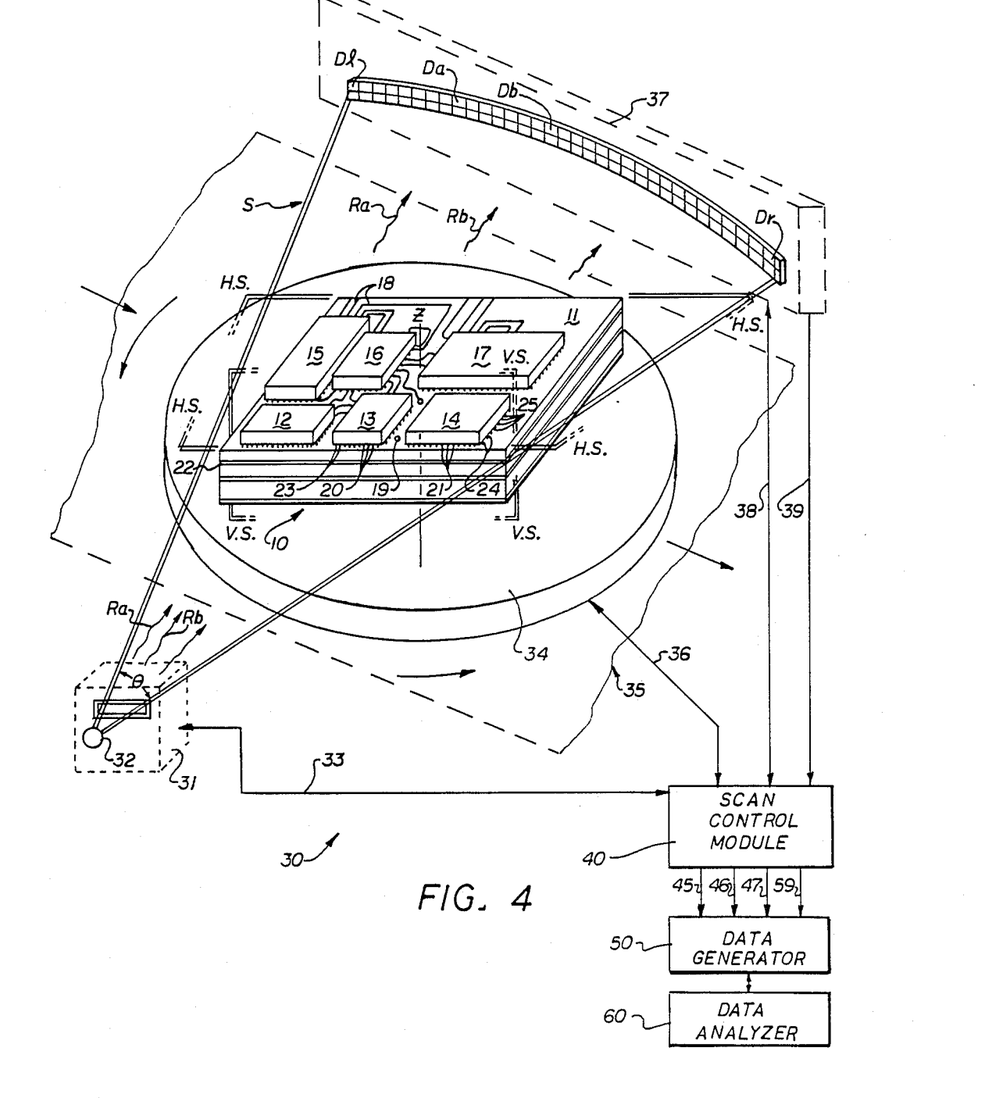
FIG. 4 is an isometric schematic view showing a radiation source radiating X-rays in a thin sheet through solder bonds of SMDs on a board supported on a mechanical positioning table, and showing data acquisition detectors disposed along the arc of the sector, and showing a scan control module.

The present invention alleviates the problem of inspecting concealed features such as mechanical/electrical interconnections and solder bonds of populated printed circuit boards or other electonic devices as shown in FIG. 4 by using a specially designed computed tomography system 30 having very high spatial resolution and including a radiation source module 31 to radiate collimated X rays R in a thin sheet fanning out in a sector S. The radiation source module 31 includes a conventional radiation source 32 such as a constant-potential X-ray tube generator, an isotopic device, or a linear accelerator. The preferred radiation source 32 is a microfocus industrial X-ray tube which is adjustable in voltage and current and produces a fan of X-rays Ra, Rb etc. Suitable alternative X-ray sources may be used, however. The beam of x rays should be collimated by the radiation source aperture to a slice thickness less than the spacing between SMD bottom surfaces and PC board 10 surface 11. The slice thickness is preferably adjustable to approximately the dimensions of a trace 18 or 22 or solder bonds 25 of interest. These dimensions can range from 20 microns to several hundred microns. The spatial resolution in the plane of the slice should be at least high enough to partially include three-to-five pixels within the width of a solder bond 25 or circuit board trace 18.

The device or board 10 to be inspected is positioned on the support table 34 in the mechanical (spatial) positioning module 35, which positions ("picks and places") the device 10 so that the X-ray sheet intersects a horizontal slice (HS) or a vertical slice (VS) through solder bonds 25 or circuit board traces 18. The features attenuate the X-rays R passing through to data acquisition module 37 radiation detectors Da, Db, etc. positioned in an arc defining the sector S centered around radiation source 32. The radiation detectors preferably comprise an array of discrete detector elements D1(left), . . . Da, . . . Db, . . . Dr(right) each having a width extending in a chord across a portion of arc $\theta$, and thereby delimiting a sector S subsector within which the discrete detector D recieves radiation. Suitable detector elements include: scintillation-crystal and photomultipler combinations, Xenon ionization chambers, or preferably scintillation crystals combined with high-performance solid-state photodiodes to provide good linearity over a wide dynamic range. Within data acquisition module 37, each detector Da, Db, etc. drives a respective detector channel including a preamplifier, offset compensator, and sampling circuitry (not shown) to measure and store levels of radiation received during selected intervals of time.

As shown in FIG. 4, the radiation source module 31 X-ray output, positioning module 35 movements, and data acquisition module 37 radiation measurement and storage operations are all controlled by a scan control module 40 computer 41. The scan control module 40 preferably also includes a data signal memory 49, an operator console 43 with an input keyboard, a hard copy printer (not shown) and a high-resolution video display 44. The console 43, via line 42, supervises the computer 41 and hence the overall operation of CT system 30. Scan control module 40 is also connected by lines 45, 46, 47 and 59 to image data generating means 50 and by lines 59 and 70 to image data analyzing means 60, as will be further described below.

Figure 5:
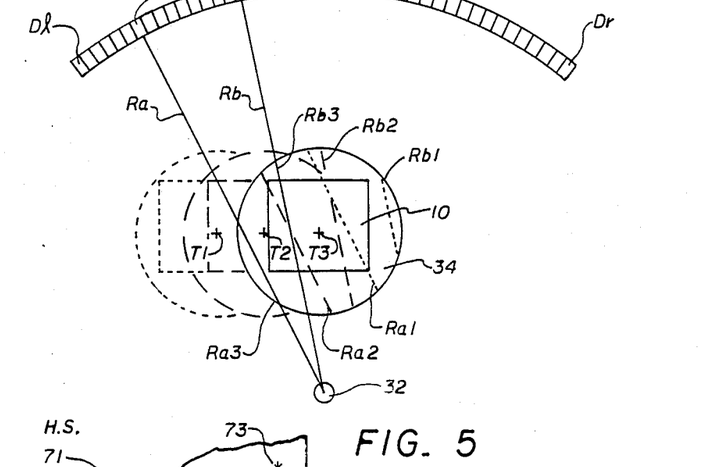
FIG. 5 is a schematic top view of the X-ray source emitting X rays in a sheet shown as comprising a discrete ray Ra which successively intersects parallel paths Ra1, Ra2, Ra3, and a discrete ray Rb which succesively intersects parallel paths Rb1, Rb2 and Rb3 through a printed wiring board or device under inspection.

When a device 10 is scanned, X rays in different subsectors pass at different angles through the device. FIG. 5, for the sake of clarity, shows subsector rays Ra and Rb as discrete lines incident upon respective detectors Da and Db. The present invention may be operated either in a "translate-rotate" mode (so-called "second generation" scanning) or in a "rotate-rotate" mode ("third generation" scanning).

Figure 6:
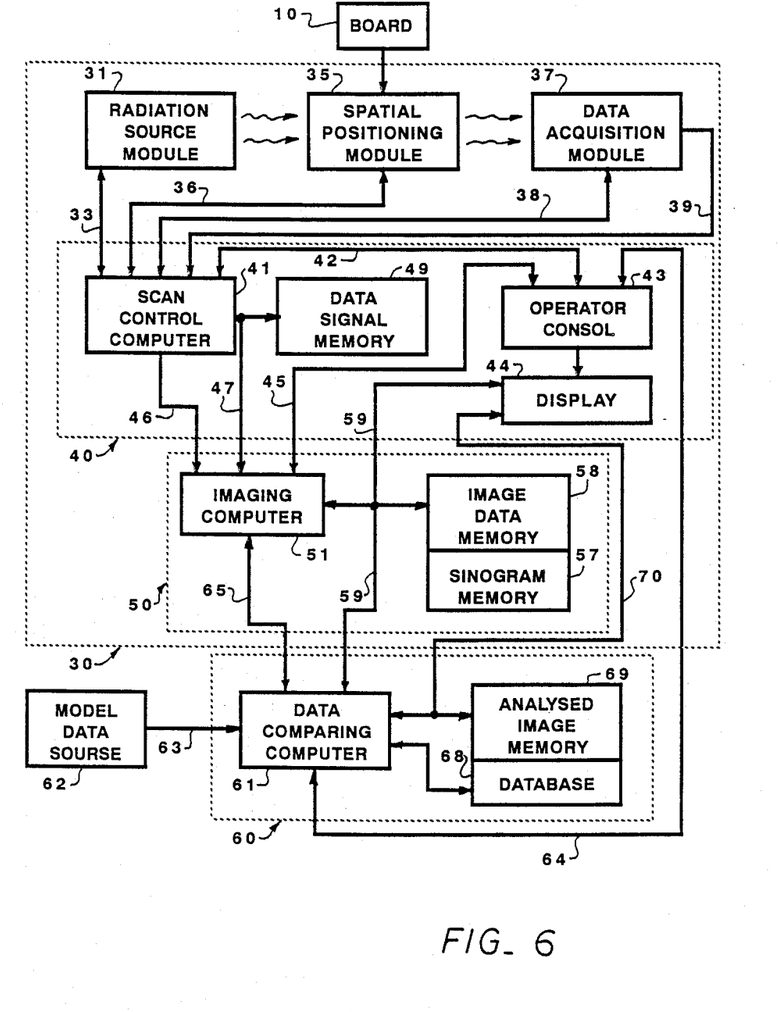
FIG. 6 is a block diagram of a CT system configuration suitable for implementing the present invention.

In operation according to the translate-rotate method, to detect and measure radiation attenuated along radial lines oriented in Cartesian coordinates which are convenient for processing by computed tomography techniques, scan control module 40 (FIG. 4) collects radiation attenuation measurements along sets of side-by-side parallel lines which are sequentially traced through device 10 as it is translated across the subsector of a given dectector. As the device 10 is translated through successive positions T1, T2, and T3 (FIG. 5), ray Ra successively passes through side-by-side parallel paths Ra1, Ra2, and Ra3, while ray Rb successively passes through parallel paths Rb1, Rb2, and Rb3. Detected radiation integrals from respective detector channels are multiplexed into an analog-to-digital converter (not shown) in scan control module 40, and the digitized measurement data signals are stored in a data signal memory 49 (FIG. 6). The parallel path measurement sets provided by all of the detectors together represent many different angles across the device 10. After the device 10 has been translated completely across sector S and measurement data signals have been stored in data memory 49, the device 10 under inspection is rotated by a selected angle, preferably equal to the sector angle, around an axis Z (FIG. 4) perpendicular to the plane of sector S and typically passing through the device 10 under inspection.

Alternately, the scan control computer 41 can operate the spatial positioning module 35 and data acquisition module 37 according to the "rotate-rotate" method as is well known to those skilled in the art of computed tomography.

Figure 7:
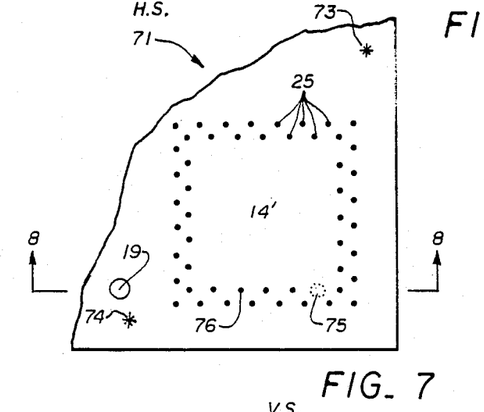
FIG. 7 is a plot of solder bond density distribution generated from values of X-rays attenuated along paths in a slice through a SMD device of FIG. 1 or 2.
Figure 8:
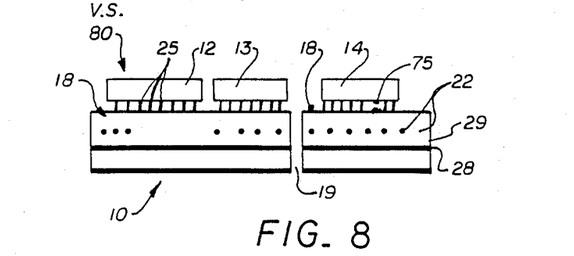
FIG. 8 represents a CT image of a vertical cross-section VS through a FIG. 3 multiple layer PCB and through selected solder bonds and traces.

For a given slice (HS or VS), when a device 10 under inspection has been scanned at all desired angles $\theta$ the measurement data signals stored in data memory 49 are transferred through a high-speed interface 47 to an image data generating module 50 as shown in FIG. 6. The image data generating module 50 includes an imaging computer 51, which can be a conventional minicomputer, and associated peripheral devices including a substantial image data (RAM) memory 58, and a secondary mass memory (not shown). The imaging computer 51 processes the measurement data signals by computed tomography techniques which are well known in the art, as explained in *Principles of Computed Tomography of The Skull and Brain* by Potts and Newton, Eds. Mosby, St. Louis (1981). Imaging computer 51 is optionally supplemented by one or more special processors (not shown) to speed generation of image data, to process previously acquired data, or to process image data, according to functions which are more complex than can be performed efficiently by an imaging minicomputer 51. The measurement data signals received from memory 49 are processed to form an intermediate sinogram which is stored in sinogram memory 57 and used by imaging computer 51 to generate two-dimensional image data representing a plot of the feature density distribution across the plane of the slice through the device 10, as shown in FIG. 7 for a plot 71 of a horizontal slice HS through good solder bonds 25, broken solder bond 75, and solder bridge 76 of area array device 14, or as shown in FIG. 8 for a plot 80 of a vertical slice VS through surface traces 18, vertical via 19, interior traces 22, solder bonds 25 and 75, ground plane 28 and fiberglass board material 29 in a multilayer board 10 as in FIG. 3.

Such two-dimensional image data can be transferred via line 59 to display 44 and the image analyzed by an operator for indications of defects in the board or device 10 under inspection. However, according to the present invention, the two dimensional density plot 71 (FIG. 7) or 80 (FIG. 8) image data are further processed to automatically quantify and evaluate defect severities, to rate overall board or device acceptability or non-acceptability, and to provide statistical data from which information about possible variations in process parameters can be deduced.

In order to automatically quantify and evaluate image data according to the present invention, a computed tomography system 30 is adapted as shown in FIG. 6 to further include image data analyzing means 60 with image data comparing computer 61. In practice, imaging computer 51 and image data comparing computer 61 may be embodied in a single "image processing computer" (not shown). Image data analyzing means 60 is first provided from data source 62 with model data for the components, interconnections and boards or other devices to be inspected, including:

(1) Board specifications of the types, locations and orientations of components and bonds or other mechanical/electrical interconnections on the board;

(2) Model board parameters including:
  a. Placement classification parameters based on bond or component size, shape and signature, which determine whether a solder bond or component misplacement excursion in image data is classified as:
    1. Missing solder or component;
    2. Misplaced/misaligned solder or component; or
    3. Extra solder.
  b. Model bond characterization parameters of:
    1. Solder density threshold;
    2. Local and total solder mass quantities; and
    3. Solder bond shape signatures.
  c. Normal position parameters for transforming image data to rotate the corresponding image so that interconnections being inspected are oriented along predetermined orthogonal axes and to translate the image to a predetermined "normal" location.

(3) Defect severity parameters for weighting detecting out-of-tolerance (out-of-compliance) component or bond defect conditions to provide defect severity variables indicating the defect significance for the respective component or bond. The defect variables are used to provide defect records of:
  a. The number of incidences of the defect;
  b. The maximum severity of incidences of the defect; and
  c. The sum of the severities of incidences of the defect.

These three defect records together form respective component and bond defect vector which are used as terms in a figure-of-merit function giving the total board defect rating.

(4) Accept/reject criteria or cut-off limits for each type of board or device being inspected, to be applied to the board defect severity rating to determine whether the overall board is acceptable.

Figure 9:
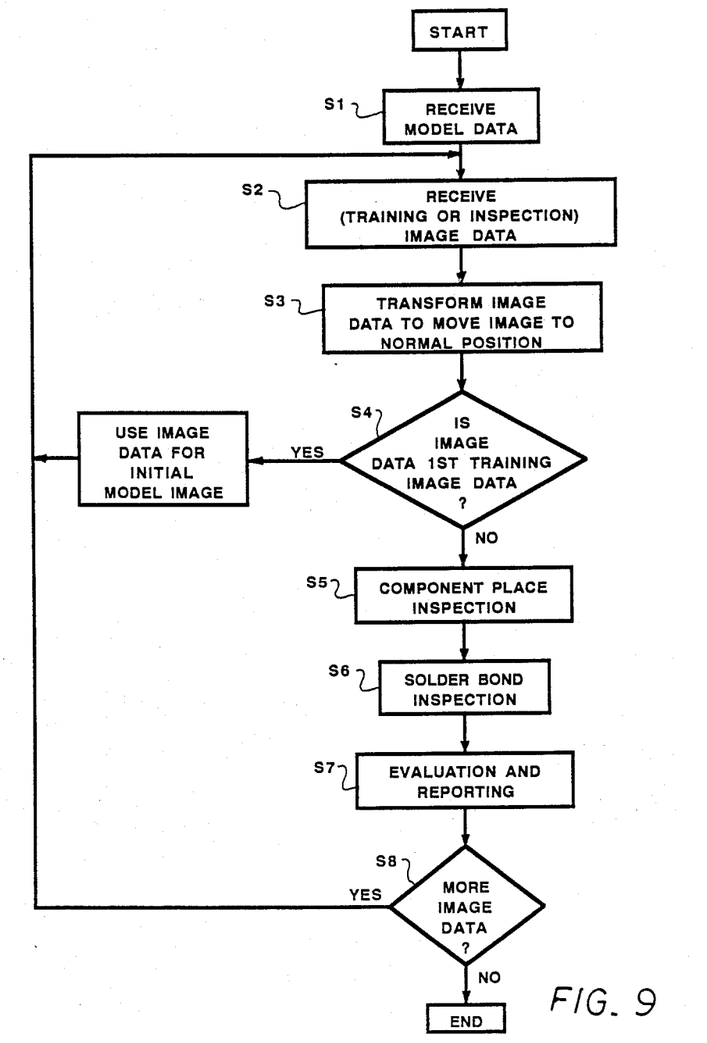
FIG. 9 is a flowchart of a preferred method of automatically analyzing input images.

As indicated in the FIG. 9 flowchart: in step S1 the image data analyzing means 60 receives on line 63 from source 62 model data including Specifications 1, Parameters 2 and 3, and Criteria 4. Then, as indicated in step S2, analyzing means 60 receives via line 59 digitized data for a training image or image portion (not shown). Next, as indicated in step S3, image data comparing computer 61 identifies alignment fiducial 73, 74 locations in the image data (FIG. 7), and determines whatever rotation and translation may be necessary to move the image to the "normal position". To minimize interpolations and to avoid reconstructing unoriented images, image data comparing computer 61, using line 65, preferably instructs imaging computer 51 to retrieve the sinogram from memory 57 and to rotate it to the normal orientation, and then to reconstruct the oriented image data. This typically saves processing time in inspections. The reproduced and oriented, but not yet shifted, image data are then provided on line 59 to the analyzing means 60 and linearly translated to the "normal position".

The first training image data are used in FIG. 9 step S4 as the initial "model image," and data comparing computer 61 returns to step S2 to repeat the process on the next training image data. Each succeeding training image data are moved to the normal position and used for "component placement inspection" as generally indicated in step S5 and as more specifically indicated in FIG. 10. Each slice image data are subtracted from the preceding model image data to give "difference image" data as shown in step 5A, and training difference image data are averaged with the preceding model image data to normalize the model image data to minimize the least squares, absolute, and total mass deviations of the model image from training images of known acceptable boards or devices. The normalized model image data are stored in database memory 68.

Figure 10:
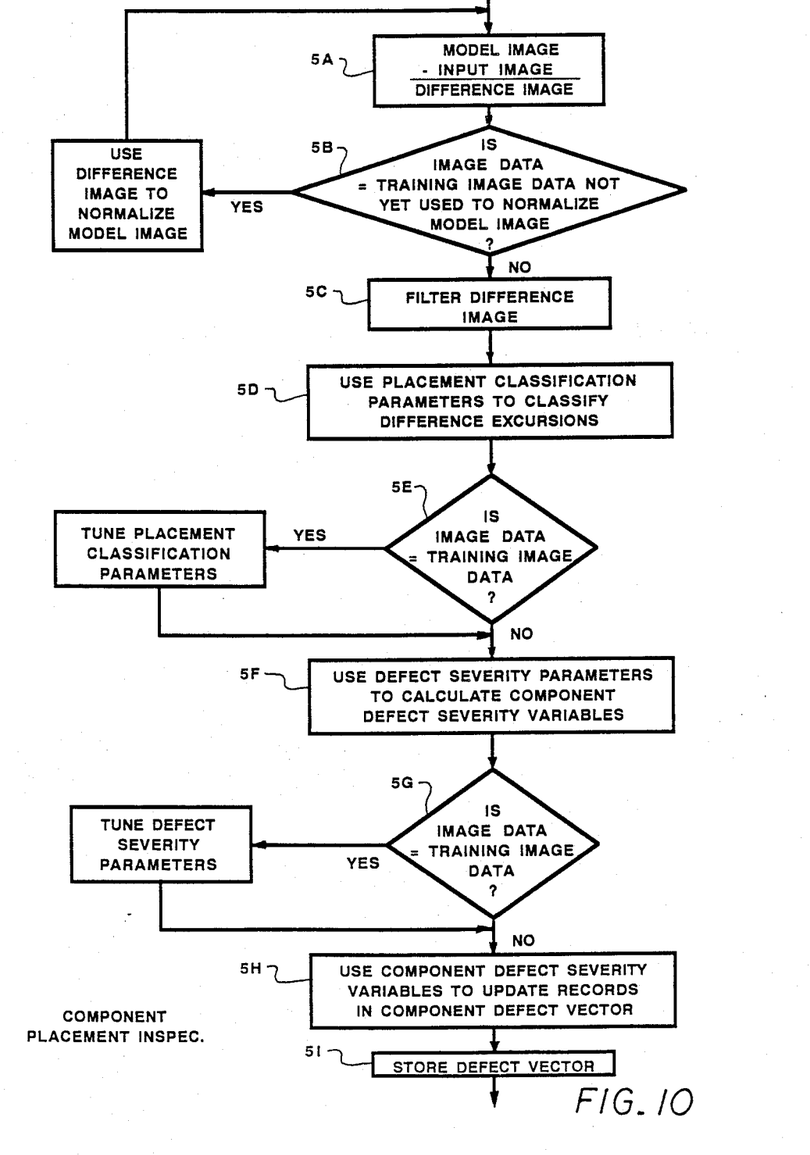
FIG. 10 is a flowchart of a preferred method of performing the FIG. 9 step of component placement inspection.

As indicated in FIG. 10 step 5B, image comparing computer 61 preferably uses the training difference image data to normalize the preceding model image data into a current model image, and, repeating step 5A, subtracts the training image data from the preceding model image to give updated training difference image data. Due to small misalignments and variations between X-ray scans, any two sets of image data, even in the normal position, will differ slightly. Therefore, as indicated in step 5C, image data comparing computer 61 filters the difference image data to reduce minor and insignificant misalignment signatures.

Both training and inspection devices are expected to have feature variations within normal manufacturing tolerances. The filtered difference image shows out-of-tolerance positive and negative differences or "excursions" between features in the analyzed image data and ing the model image data. As indicated in step 5D, image comparing computer 61 identifies and measures feature excursions, and, depending on the placement classification parameters for the identified component or bond, classifies excursions as representing either (1) missing components or solder bonds; (2) misplaced/-misaligned components or solder bonds; or (3) extra components or solder bonds. For training image data, as indicated in step 5E, the placement classification parameters are "tuned" so that, through experience, image data comparing computer 61 learns to classify training images to agree with predetermided classifications. In step 5F, classified defects are weighted by respective defect severity parameters to produce defect severity variables. For training images, in step 5G, image data comparing computer 61 tunes the database 68 defect severity parameters to produce variables agreeing with predetermined defect severity variables. In step 5H, image data comparing computer 61 uses the component defect severity variables to update the three defect records forming the component defect vector, and, in step 5I, stores the defect vector in the database memory 68.

Figure 11:
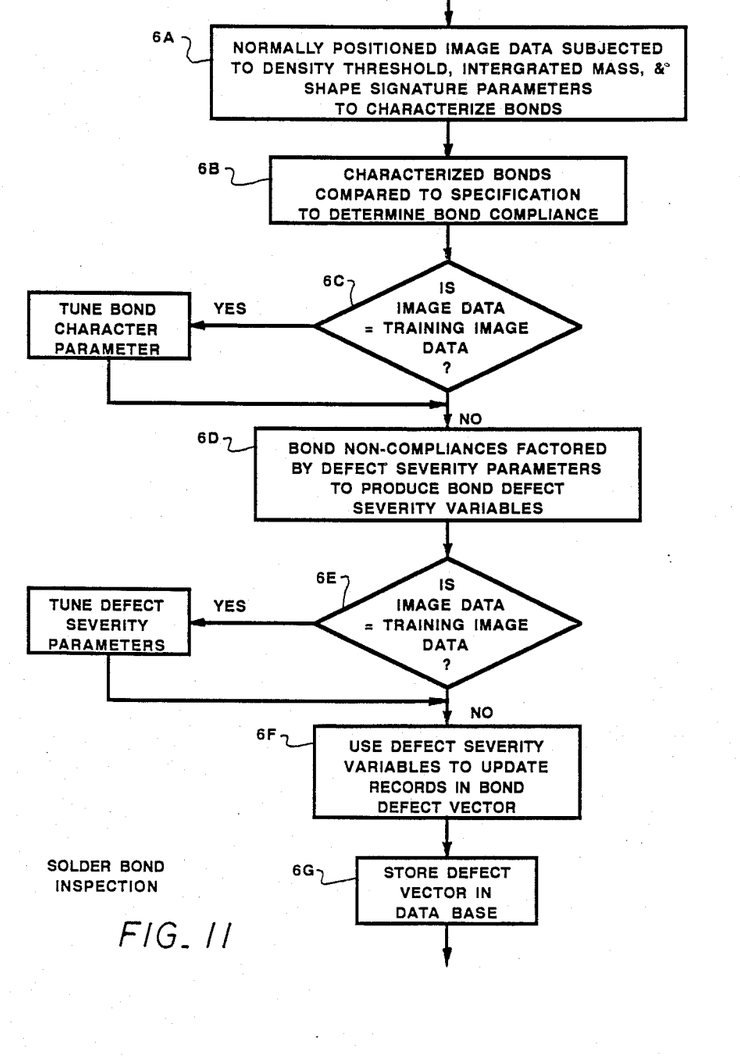
FIG. 11 is a flowchart of a preferred method of performing the FIG. 9 step of solder bond inspection.

In the "solder bond inspection" step, as generally indicated in FIG. 9 step S6, and as more specifically indicated in FIG. 11, normally positioned image data in FIG. 11 step 6A are processed according to the model bond density threshold parameter and the shape signature parameter to distinguish solder-filled regions, and the local and total model bond mass parameters are used to quantify solder bond characteristics. In step 6B, characterized bonds are compared to, to determine their compliance with, the board specifications for bond types, locations and orientations. For training images (step 6C), the bond parameters are tuned so that the bond complies to the board specifications. Then, (step 6D) non-compliances are weighted by the bond defect severity parameters to provide bond defect severity variables. For training images (step 6E), the bond defect severity parameters are tuned. In step 6F, image data comparing computer 61 uses the bond defect severity variables to update the three defect records forming the bond defect severity vector, and in step 6G, stores the defect vector in database memory 68. Alternately, the solder bond inspection step of FIG. 11 could be performed before the component placement inspection step of FIG. 10.

Figure 12:
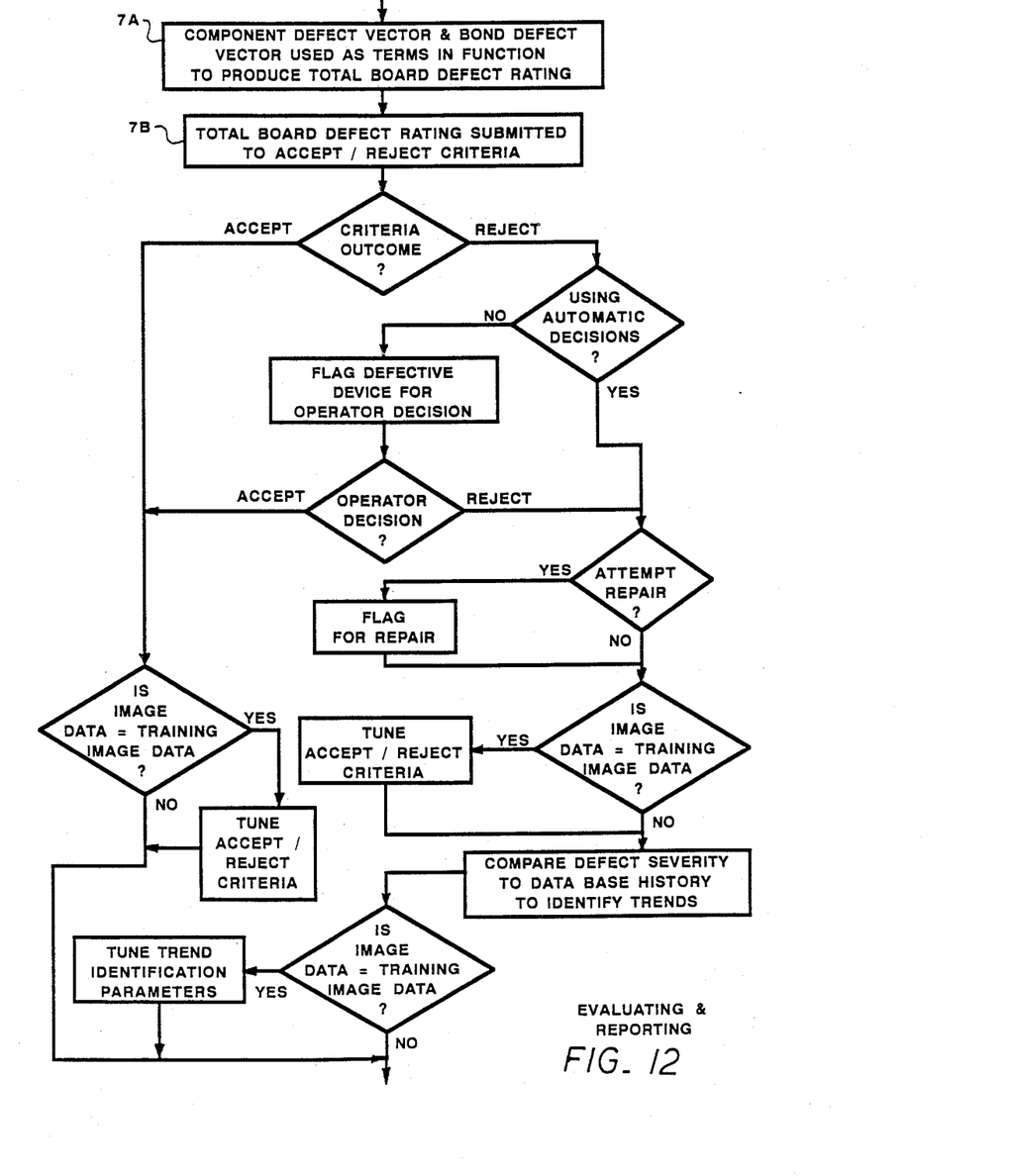
FIG. 12 is a flowchart of a preferred method of performing the FIG. 9 step of evaluating and reporting.

In the step of "evaluating and reporting", as generally indicated in FIG. 9 step S7, and as more specifically indicated in FIG. 12, the component defect vector and the bond defect vector are combined in step 7A, in a figure-of-merit function to give a total board (or device) defect rating which, in step 7B, is subjected to the accept/reject criteria to indicate whether the board will be either:

(1) Accepted;
(2) Rejected; or
(3) Optionally flagged for an operator decision to accept, reject or repair the board.

Image data comparing computer 61 can be programmed to decide whether a device should be repaired.

For training images, the accept/reject criteria are tuned to indicate predetermined acceptance, rejection or flagging.

The total board defect rating is compared to the database 68 history of board defect ratings to identify trends indicative of production line faults. For training images. trend identification parameters are tuned.

Once training images have been processed to provide a normalized model board image, tuned component classification and defect severity parameters, tuned bond characterization and defect severity parameters, tuned accept/reject criteria and tuned production fault identification parameters, and to establish confidence levels for the accept/reject/repair decisions, a CT system 30 with image data analyzing means 60 according to the invention is prepared to automatically analyze inspection image data.

Returning to repeat FIG. 9 step S2, inspection image data is input to the image data comparing computer 61, and then steps S3 through S8 are repeated in the same way as for training images, except without "tuning" parameters and criteria. The opertor console 43 is further used to control reconstructed image data comparison and display, display image contrast/latitude (i.e. gray or color level), several types of mensurations, region-of-interest statistics, and optionally image portion zoom and pan.

Although the present invention has been described above in terms of a particular preferred embodiment, it will be appreciated by those skilled in the art that alterations and modifications thereof may be made without departing from the essence of the invention. It is therefore intended that the appended claims be interpreted as covering any and all such alterations and modifications as fall within the true spirit and scope of the invention.

What is claimed is:

1. A method of inspecting mechanical/electrical interconnections between electronic components and conductors on a supporting circuit board, comprising the steps of:

arranging radiation source means to radiate X-rays along and about a plane in a thin sheet through a sector defined by said source means and by an arc lying in said plane, centered on said source means, and located at a selected radius from said source means;

arranging X-ray detector means in said plane in a linear array coinciding with said arc to receive X-rays from said source means;

positioning said board so that said mechanical/electrical interconnections are intersected by said plane while operating said detector means to detect levels of radiation received from said source means during predetermined time intervals and to develop corresponding measurement data signals, and storing said measurement data signals;

rotating said board by a selected angle $\theta$ around an axis normal to said plane;

repeating a selected number of times said steps of operating said detector means, storing said measurement data signals, and rotating said board;

processing said stored measurement data signals by computed tomography techniques to generate image data corresponding to an image of the density distribution of said mechanical/electrical interconnections intersected by said plane; and comparing said image data to model data to develop defect data indicative of defects in said mechanical/electrical interconnections.

2. A method as in claim 1 wherein said step of positioning includes positioning said board so that said mechanical/electrical interconnections are intersected by said plane outside of said sector, said step of positioning is followed by a step of translating said board in a selected direction through said sheet of X rays across said sector, and said step of repeating includes the step of translating said board before operating said detector means.

3. A method as in claim 1 wherein said mechanical/electrical interconnections include solder bonds, and wherein said step of comparing comprises the steps of:
(1) receiving model data including position parameters, defect parameters, and acceptance criteria for the board under inspection;
(2) receiving said image data;
(3) transforming said image data using said position parameters so that its corresponding image is moved to a normal position;
(4) if said image data is for a first training image, then using said image data for model image data and repeating steps 2 and 3;
(5) inspecting the placement of said components represented by said image data using said position and defect parameters to develop component defect severity variables;
(6) inspecting said solder bonds represented by said image data to develop bond defect severity variables; and
(7) evaluating said defect variables using said defect parameters and acceptance criteria to develop board defect data.

4. A method as in claim 3 wherein said steps 2 through 7 are executed on image data for at least one model board image and are then executed on image data for at least one board under inspection which corresponds to said model board.

5. A method as in claim 4 wherein said step 5 of inspecting the placement of said components comprises the steps of:
(A) subtracting the image data from the model image data to provide difference image data;
(B) if the image data is training image data not yet used to normalize the model image data, then using the difference image data to normalize the model image data and repeating step A;
(C) filtering the difference image data to eliminate insignificant misalignment signatures;
(D) using placement classification parameters to classify difference image data excursions;
(E) if the image data is training image data then tuning the placement classification parameters;
(F) using defect severity parameters to calculate component defect severity variables;
(G) if the image data is training image data then tuning defect severity parameters;
(H) using component defect severity variables to update records in a component defect vector; and
(I) storing the defect vector.

6. A method as in claim 4 wherein said model data includes model bond geometry specifications and parameters for solder density threshold, mass and shape signature, and wherein said step 6 of inspecting said solder bonds comprises the steps of:
(A) subjecting the normally positioned image data to model bond parameters to characterize the bonds;
(B) comparing characterized bonds to said specifications to determine bond geometry compliance;
(C) if the image data is for a training image then tuning the bond character parameters;
(D) using defect severity parameters to factor bond non-compliances to develop bond defect severity variables;
(E) if the image data is for a training image, then tuning defect severity parameters;
(F) using the defect severity variables to update records in a bond defect vector; and
(G) storing the defect vector.

7. A method as in claim 4 wherein said step 7 of evaluating comprises the steps of:
(A) applying said acceptance criteria to said board defect data to decide whether to accept, attempt repair of, or reject a board;
(B) using defect vectors to identify trends in board manufacturing problems; and
(C) producing an overall board defect rating signal.

8. Means for inspecting mechanical/electrical interconnections between electronic components and conductors of a supporting circuit board, comprising:
radiation source means for radiating a thin sheet of X rays along a selected plane in a sector;
spatial positioning means for positioning said circuit board with said interconnections in said plane and in said sector;
data acquisition means for detecting levels of radiation received from said source means and for developing corresponding measurement data signals;
scan control means for controlling operation of said source means, said positioning means and said data acquisition means, and including data storage means for receiving and storing said measurement data signals;
image data generating means responsive to measurement data signals from said data storage means, and operative to generate image data corresponding to an image of the density distribution of said mechanical/electrical interconnections intersected by said plane; and image data analyzing means including database means for storing model data for said mechanical/electrical interconnections and including image data comparing means for comparing said image data to said model data to develop defect data indicative of defects in said mechanical/electrical interconnections.

9. Means as in claim 8 wherein said image data analyzing means comprises means for inspecting component placement and for producing component defect variables;

means for inspecting solder bonds and for producing bond defect variables; and means for evaluating said component defect and bond defect variables to produce an overall board defect rating signal.

* * * * *

UNITED STATES PATENT AND TRADEMARK OFFICE
Certificate

Patent No. 4,852,131                                                                Patented: July 25, 1989

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is:
Robert A. Armistead and James H. Stanley.

Signed and Sealed this Fourth Day of December 1990.

EDWARD P. WESTIN

*Supervisory Patent Examiner*
*Group Art Unit 256*